United States Patent
Momose et al.

(10) Patent No.: US 11,271,161 B2
(45) Date of Patent: Mar. 8, 2022

(54) GAS SENSOR, GAS MEASUREMENT APPARATUS, FABRICATION METHOD FOR GAS SENSOR AND HYDROGEN SULFIDE CONCENTRATION MEASUREMENT METHOD

(71) Applicant: FUJITSU LIMITED, Kawasaki (JP)

(72) Inventors: Satoru Momose, Atsugi (JP); Michio Ushigome, Atsugi (JP); Osamu Tsuboi, Kawasaki (JP)

(73) Assignee: FUJITSU LIMITED, Kawasaki (JP)

( * ) Notice: Subject to any disclaimer, the term of this patent is extended or adjusted under 35 U.S.C. 154(b) by 879 days.

(21) Appl. No.: 16/048,849

(22) Filed: Jul. 30, 2018

(65) Prior Publication Data
US 2019/0067585 A1    Feb. 28, 2019

(30) Foreign Application Priority Data

Aug. 22, 2017    (JP) .............................. JP2017-159215

(51) Int. Cl.
| | | |
|---|---|---|
| *H01L 51/05* | (2006.01) | |
| *H01L 51/00* | (2006.01) | |
| *G01N 33/00* | (2006.01) | |
| *G01N 27/12* | (2006.01) | |

(52) U.S. Cl.
CPC ....... *H01L 51/0037* (2013.01); *G01N 27/125* (2013.01); *G01N 33/0044* (2013.01); *H01L 51/004* (2013.01); *H01L 51/002* (2013.01)

(58) Field of Classification Search
CPC ............. G01N 27/125; G01N 33/0044; H01L 51/002; H01L 51/0037; H01L 51/004
See application file for complete search history.

(56) References Cited

U.S. PATENT DOCUMENTS

| | | | | |
|---|---|---|---|---|
| 5,215,820 A | * | 6/1993 | Hosokawa ........... | C08G 61/123 428/328 |
| 2008/0166549 A1 | * | 7/2008 | Shieh ................... | C09D 165/00 428/336 |

FOREIGN PATENT DOCUMENTS

| | | |
|---|---|---|
| JP | 5-87758 A | 4/1993 |
| JP | 11-23508 A | 1/1999 |
| JP | 2008-216038 A | 9/2008 |

OTHER PUBLICATIONS

Lauque et al., "Highly sensitive and selective room temperature $NH_3$ gas microsensor using an ionic conductor (CuBr) film", Anal. Chim. Acta 515, May 25, 2004, pp. 279-284 (6 pages).

* cited by examiner

*Primary Examiner* — Mark Kopec
*Assistant Examiner* — Jaison P Thomas
(74) *Attorney, Agent, or Firm* — Westerman, Hattori, Daniels & Adrian, LLP

(57) ABSTRACT

A semiconductor material includes polythiophene, sulfonic acid, and copper ion. The copper ion is bonded to the sulfonic acid.

11 Claims, 10 Drawing Sheets

FIG. 12A
FIG. 12B
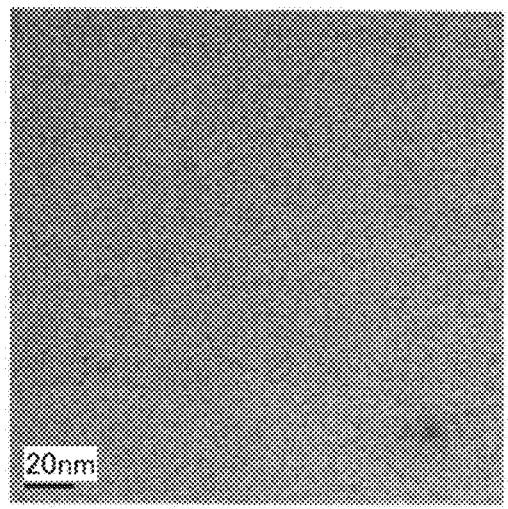
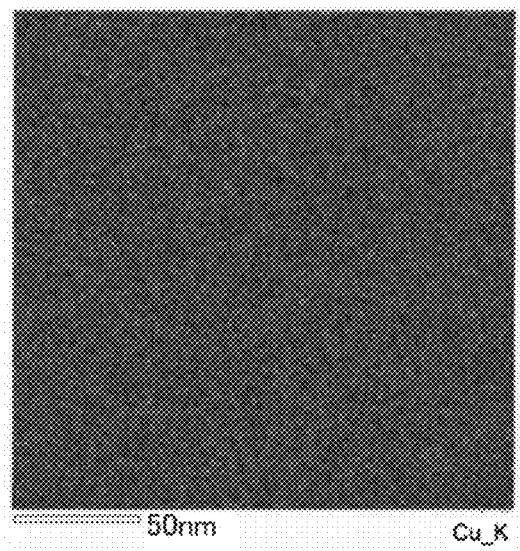

GAS SENSOR, GAS MEASUREMENT APPARATUS, FABRICATION METHOD FOR GAS SENSOR AND HYDROGEN SULFIDE CONCENTRATION MEASUREMENT METHOD

CROSS-REFERENCE TO RELATED APPLICATION

This application is based upon and claims the benefit of priority of the prior Japanese Patent Application No. 2017-159215, filed on Aug. 22, 2017, the entire contents of which are incorporated herein by reference.

FIELD

The embodiments discussed herein are related to a semiconductor material, a gas sensor, a gas measurement apparatus, a fabrication method for semiconductor material and a hydrogen sulfide concentration measurement method.

BACKGROUND

A gas measurement apparatus (gas sensor) that is in the main stream at present is configured such that variation of electric resistance arising from adsorption of a chemical material to the surface of a semiconductor (semiconductor material) represented, for example, by tin dioxide is measured. In order to perform high-sensitivity measurement of gas by a gas measurement apparatus having such a configuration as just described, it is demanded to supply current using constant current power supply and control heating such that the temperature of a device is controlled to a region in which a good detection characteristic is obtained.

Therefore, for example, power consumption of the detection circuit is liable to become high and a great amount of power is consumed by a heater for heating the device. Further, a gas measurement apparatus of the type described above indicates a similitude response to many kinds of gas if the gas contacting with a gas sensor (gas sensor device) is reducing gas. Therefore, it is difficult to know to which kind of gas the response of the gas sensor is.

SUMMARY

According to one aspect of the embodiment, a semiconductor material includes polythiophene, sulfonic acid, and copper ion, wherein the copper ion is bonded to the sulfonic acid.

The object and advantages of the invention will be realized and attained by means of the elements and combinations particularly pointed out in the claims. It is to be understood that both the foregoing general description and the following detailed description are exemplary and explanatory and are not restrictive of the invention.

BRIEF DESCRIPTION OF DRAWINGS

FIGS. 12A and 12B are views depicting an example of an image of a detection material film surface produced under similar conditions to those of the gas sensor of the present embodiment in the proximity of the center in a thickness wise direction by a typical scanning transmission electron microscope and an example of mapping of an EDS signal corresponding to the K shell of Cu with respect to a same field of view;

DESCRIPTION OF EMBODIMENTS

Figure 1A:
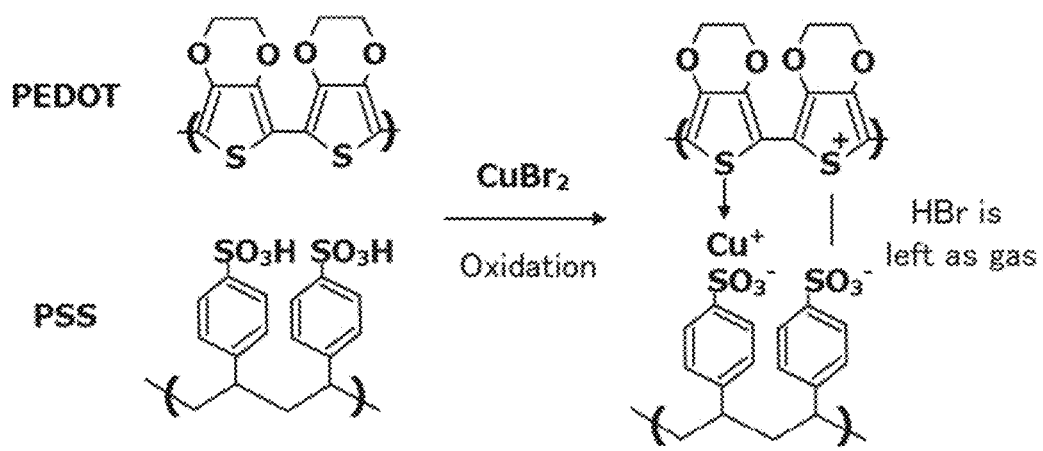
FIGS. 1A and 1B are views illustrating a formation process by a chemical reaction of a detection material in a gas sensor of an embodiment.

Incidentally, it is possible to configure a gas sensor of the resistance variation type that operates at an ordinary temperature (room temperature) and also a detection material that indicates a selective response to a specific kind of gas is available. In particular, copper (I) bromide (CuBr) of a p-type semiconductor that is a kind of copper halide is a representative of such a detection material as just described. For example, a gas sensor that selectively indicates a great electric resistance variation at a room temperature to ammonium in the atmosphere using CuBr as a detection material is disclosed in P. Lauque et al., "Highly sensitive and selective room temperature NH3 gas microsensor using an ionic conductor (CuBr) film," Anal. Chim. Acta 515 (2004), pp. 279-284, May 25, 2004.

Further, though not common in the present circumstances, also a gas sensor (sensor device) in which an organic semiconductor is used as a detection material is available. For example, an example in which polythiophene that is an organic semiconductor is used as a detection material and another example in which a detection material produced by doping polythiophene with ferric chloride is used are disclosed in Japanese Laid-Open Patent Application No. 11-023508. It is to be noted that it is not disclosed in Japanese Laid-Open Patent Application No. 11-023508 whether or not a gas sensor indicates selectivity to a specific kind of gas.

It is to be noted that various proposals have been made for a gas sensor and a gas measurement apparatus in which a semiconductor material is used.

As described above, for example, CuBr is available as a detection material for a gas sensor that selectively responds to ammonium with high sensitivity. However, a detection material for a gas sensor that similarly indicates a high degree of selectivity to different kinds of gas and has a high speed performance capable of performing measurement, for example, in one minute is not known.

For example, while one of common toxic gases that are included in volcanic gas or the like is hydrogen sulfide, also an opinion is presented that hydrogen sulfide is generated also from the inside of the human body, for example, in relation to alveolar pyralia, colitis and so forth. Therefore, a semiconductor material, a gas sensor, a gas measurement apparatus and so forth are demanded by which measurement target gas in gas such as, for example, hydrogen sulfide can be selectively detected at a high speed and with high sensitivity.

First, a case in which hydrogen sulfide is measured is described as an example of measurement of measurement target gas in gas before examples of a semiconductor material, a gas sensor, a gas measurement apparatus, a fabrication method for a semiconductor material and a hydrogen sulfide concentration measurement method are described in detail.

First, hydrogen sulfide has ability of reversibly forming coordinate bonds to various metal atoms or metal ions. However, since some other gas species have coordination ability for metal atoms or metal ions, formation of coordinate bonds is performed competitively among such gas species.

Accordingly, it is possible in principle to improve the gas species selectivity by providing a mechanism for preventing approach of molecules other than those of a specific gas species around metal atoms or metal ions described above. For example, although not only ammonium but also hydrogen sulfide can be coordinated on monovalent copper ions, ammonium molecules can be bonded preferentially to acidic functional groups by disposing acidic functional groups around them. As a result, hydrogen sulfide can be bonded preferentially to copper ions, namely, monovalent copper ions can react selectively with hydrogen sulfide.

Incidentally, in order to allow a function as a gas sensor to be implemented, generation of an electric signal such as variation of electric resistance as a result of a chemical interaction described above is demanded. Therefore, an organic semiconductor or organic acid and copper ion are used such that monovalent copper ions and the organic semiconductor electronically interact with each other and the organic acid is disposed around the monovalent copper ions to allow an electric signal to be extracted.

Here, as a conductor for extracting the electric signal, it is preferable to use, for example, a semiconductor material whose carrier concentration is liable to vary by a great amount. However, it is demanded that, on the surface of the semiconductor material, copper ions electronically interact with each other without diffusing into the inside of the semiconductor material and besides acid is disposed around the copper ions. It is difficult to use an inorganic semiconductor material to implement such a function as just described.

Therefore, it is conceivable to use an organic semiconductor material and organic acid capable of interacting with the organic semiconductor material and form a composite by adding copper ions to them to produce a detection material. For formation of a good composite of the materials, it is preferable to use a method of mixing them in aqueous solution. In other words, it is desirable to use an aqueous organic semiconductor, and, as an example, poly (3,4-ethylene dioxythiophene: hereinafter referred to also as PEDOT) can be listed.

On the other hand, as the organic acid to be combined with an organic semiconductor, it is desirable to use strong acid that strongly interacts with ammonium, and, especially, for example, poly (4-styrene sulfonic acid: hereinafter referred to also as PSS), which indicates actual results in combination with PEDOT, is preferable. It is to be noted that, as the organic acid, aqueous sulfonic acid such as methanesulfonic acid or toluene sulfonic acid can be used similarly because it has no significant difference in chemical properties from PSS.

In order to add monovalent copper ions to the example of the combination material of an organic semiconductor and organic acid described above, for example, a technique of mixing bivalent copper halide into aqueous solution produced by mixing the organic semiconductor and the organic acid described above can be applied. In particular, bivalent copper ions generated from bivalent copper halide change to monovalent copper ions by oxidation of PEDOT and bond to sulfonic groups.

Since weak coordinate bonds of PEDOT whose thiophene ring can be formed on such monovalent copper ions, holes are injected from the copper ions into PEDOT molecules through the bonds. Further, as the copper halide, for example, copper (II) fluoride, copper (II) chloride, copper (II) bromide and copper (II) iodide can be listed.

Here, halide ions liberated when copper ions are reduced from bivalent to monovalent react with protons the sulfonic acid has to generate hydrogen halide. Therefore, for example, when copper (II) fluoride that generates hydrogen fluoride having high toxicity and copper (II) iodide that generates hydrogen iodide having high reducibility are used, it is preferable to take a countermeasure for reducing or isolating the toxicity.

Figure 1B:
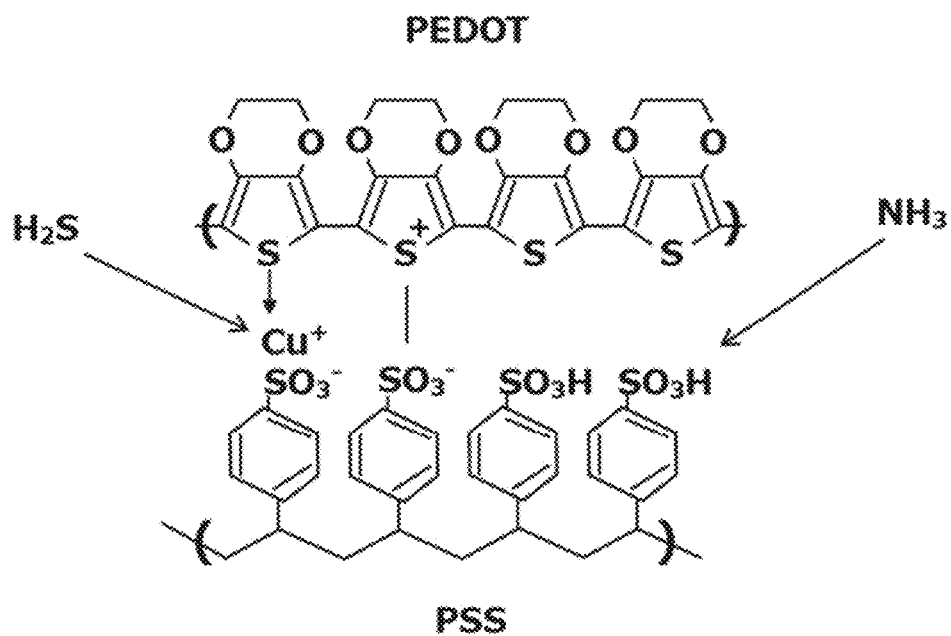

In the following, an example of a semiconductor material, a gas sensor, a gas measurement apparatus, a fabrication method for a semiconductor material and a hydrogen sulfide concentration measurement method is described in detail with reference to the drawings. FIGS. 1A and 1B are views illustrating a detection material (semiconductor material) in the gas sensor of the present embodiment. Here, FIG. 1A is a view illustrating a formation process by a chemical reaction of the detection material and depicts a process in which copper (II) bromide ($CuBr_2$) is used as oxidizer for a base (substrate) configured from PEDOT and PSS to form a composite material including monovalent copper ions.

As depicted in FIG. 1A, copper (II) bromide oxidizes PEDOT (poly (3,4-ethylene dioxythiophene)) as oxidizer and copper ions changed to monovalent are bonded to sulfonic acid groups of PSS (poly (4-styrene sulfonic acid)). Further, bromide ions are bonded to protons generated from the sulfonic acid groups to form hydrogen bromide (HBr), which is disengaged as gas. Furthermore, the sulfonic acid groups whose protons are deprived are statistically bonded to positive electric charge in the PEDOT generated as a result of oxidation.

FIG. 1B is a view illustrating selectivity between ammonium and hydrogen sulfide of the detection material depicted in FIG. 1A. If ammonium ($NH_3$) that is basic gas contacts with the detection material generated as described hereinabove with reference to FIG. 1A, then the ammonium interacts preferentially with the sulfonic acid groups having strong acidity. Therefore, an interaction between monovalent copper ions and ammonium becomes difficult (refer to the right side in FIG. 1B).

On the other hand, hydrogen sulfide ($H_2S$) that is acidic gas has a poor interaction with sulfonic acid groups and therefore interact readily with monovalent copper ions (refer to the left side in FIG. 1B). Furthermore, since an interaction between copper ions and hydrogen sulfide occurs in place of an interaction between copper ions and PEDOT, provision of holes from copper ions to PEDOT is not performed anymore and the resistance of the PEDOT increases. Consequently, the resistance of the detection body (detector; detection material) increases.

From the foregoing, a high-sensitivity gas sensor (gas measurement apparatus) that selectively reacts with hydrogen sulfide can be implemented. Further, since an interaction between copper ions and hydrogen sulfide is an equilibrium reaction that is formation of coordination bonds, for example, at an initial stage, the speed decreased by the interaction between PEDOT and copper ions changes in proportion to the hydrogen sulfide concentration. This signifies that it is possible to convert the hydrogen sulfide concentration on the basis of resistance variation in an initial response region. Therefore, measurement of the concentration can be performed at a high speed without waiting that a saturation equilibrium state of the PEDOT and copper ions is established.

Figure 2:
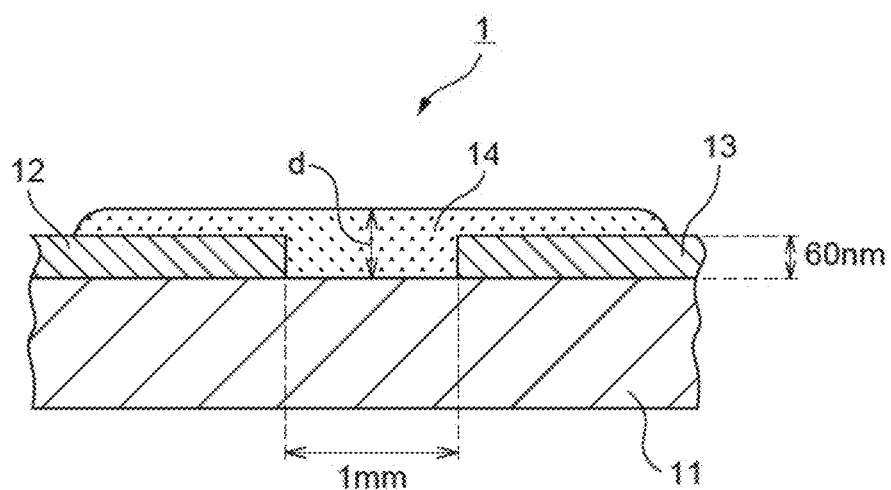
FIG. 2 is a sectional view schematically depicting an example of the gas sensor of the present embodiment.

FIG. 2 is a sectional view schematically depicting an example of the gas sensor of the present embodiment. As depicted in FIG. 2, the gas sensor 1 includes, for example, a substrate 11, two gold (Au) electrodes 12 and 13 provided on the substrate 11 and a detection body (semiconductor material) 14 provided so as to cover the Au electrodes 12 and 13. Here, the detection body 14 is solution of PEDOT:PSS obtained by mixing copper (II) bromide by 113 mg into aqueous solution of approximately 1.3 weight % of PEDOT: PSS (for example, Clevios (registered trademark) PVPAI 4083: product name: by Heraeus) by 5.0 mL such that copper (II) bromide is dissolved at a ratio of 0.1 mol/L.

The substrate 11 is, for example, a silicon wafer with a heat oxidation film (thermal oxide film thickness 100 nm) of 15 mm square, and the two Au electrodes 12 and 13 individually having, for example, a width of 5 mm, a length of 6 mm and a thickness of 60 nm are formed at a distance of 1 mm using vapor deposition. Further, the solution (detection body) 14 of PEDOT:PSS described above is provided so as to couple the two Au electrodes 12 and 13 to each other such that it is applied and naturally dried, for example, to an approximately 5 mm square size.

After the solution 14 of PEDOT:PSS is applied and dried naturally, the surface is cleaned using ethanol and then dried naturally to produce the gas sensor 1. Here, the thickness d of the detection body 14 is set, for example, to 500 nm or less. It is to be noted that the gas sensor is not limited to the gas sensor 1 depicted in FIG. 2 and naturally may be a gas sensor having various configurations to which the detection body 14 of the semiconductor material (detection material) of the present embodiment is applied.

A response (reaction) of the gas sensor 1 to various gases (measurement target gases) was evaluated by placing the gas sensor 1 described above into an air flow and changing over the gas source between pure air and one of various kinds of air including one of hydrogen sulfide of a concentration of 0.8 ppm, ammonium of a concentration of 0.9 ppm, ethanol of a concentration of 20 ppm and acetone of a concentration of 20 ppm. Here, the temperature of the used air was approximately 23° C. and the relative humidity was approximately 43%.

Figure 3:
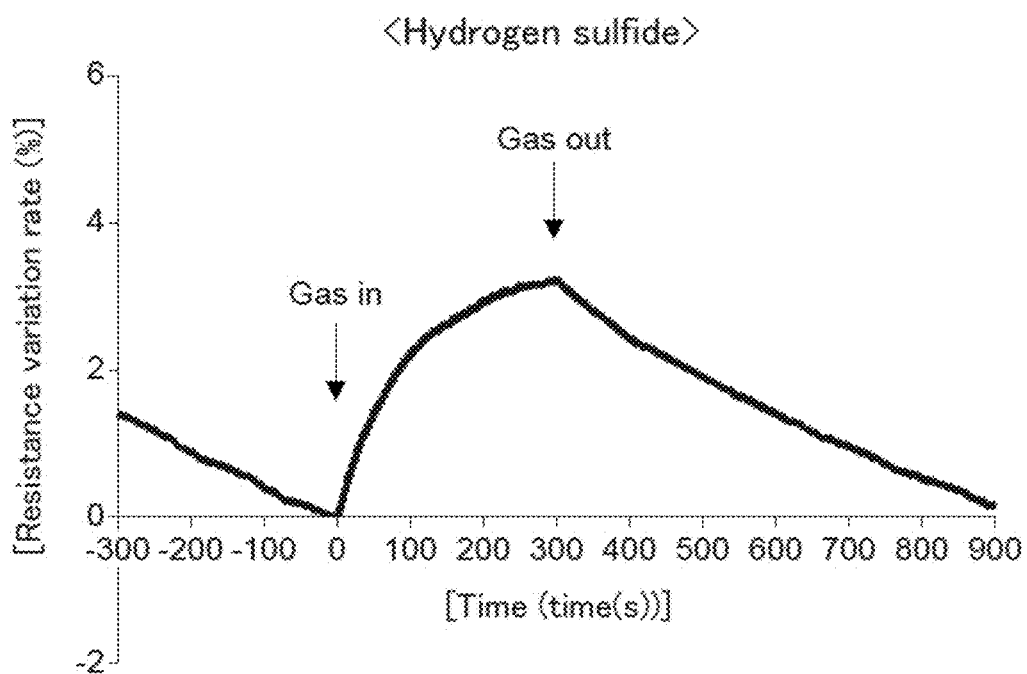
FIG. 3 is a view depicting an example of a response profile of the resistance of the gas sensor of the present embodiment to hydrogen sulfide whose atmospheric concentration is 0.8 ppm.
Figure 4:
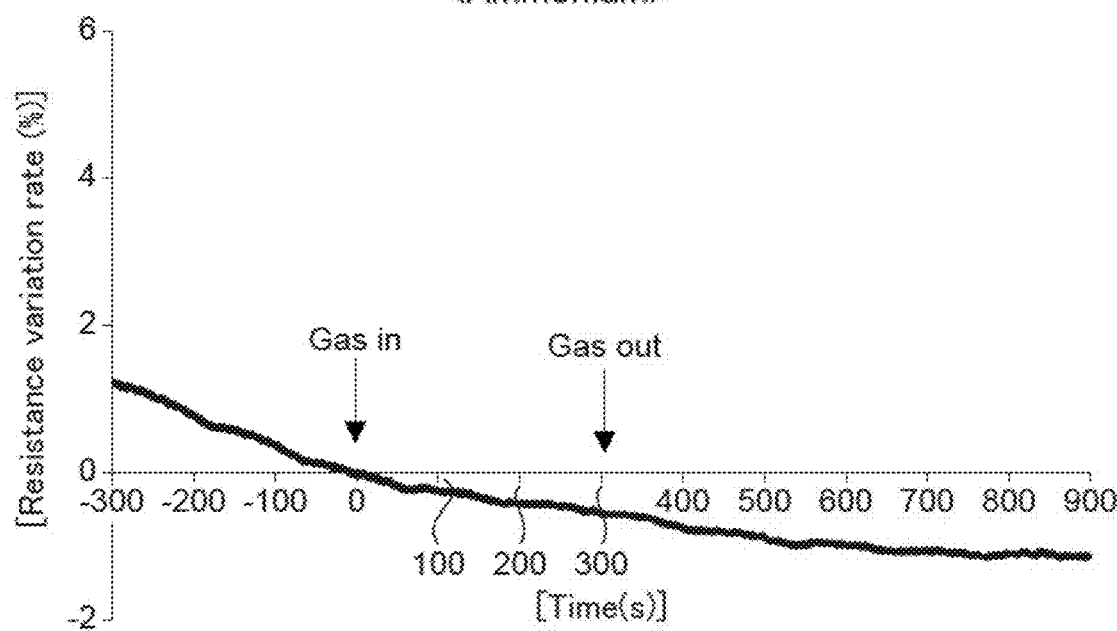
FIG. 4 is a view depicting an example of a response profile of the resistance of the gas sensor of the present embodiment to ammonium whose atmospheric concentration is 0.9 ppm.
Figure 5:
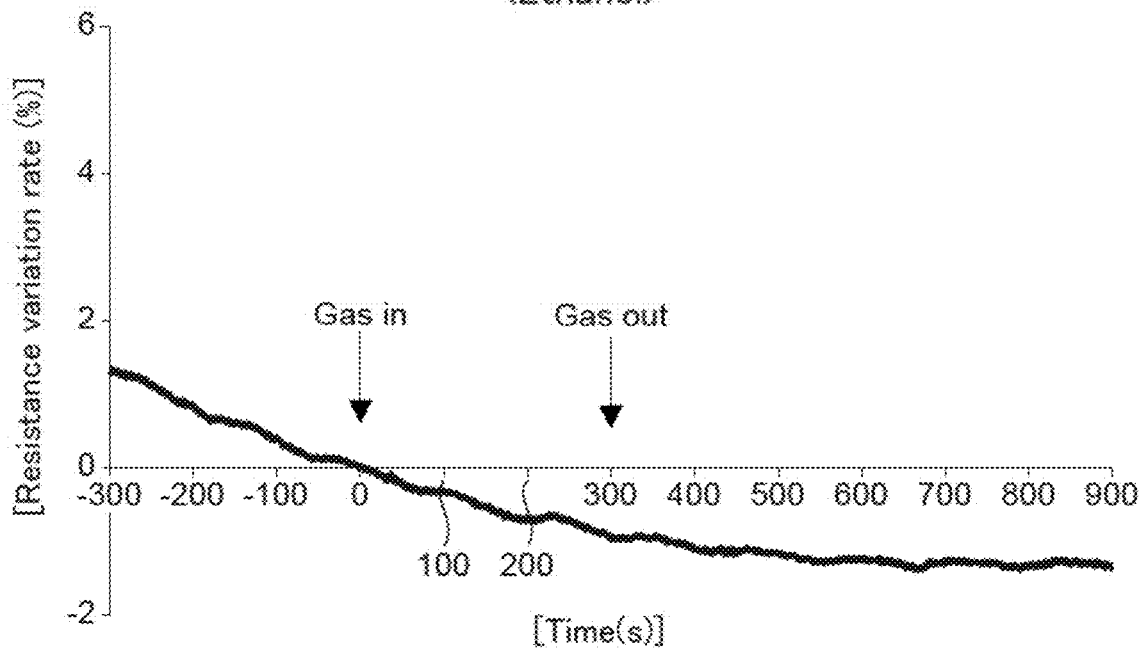
FIG. 5 is a view depicting an example of a response profile of the resistance of the gas sensor of the present embodiment to ethanol whose atmospheric concentration is 20 ppm.
Figure 6:
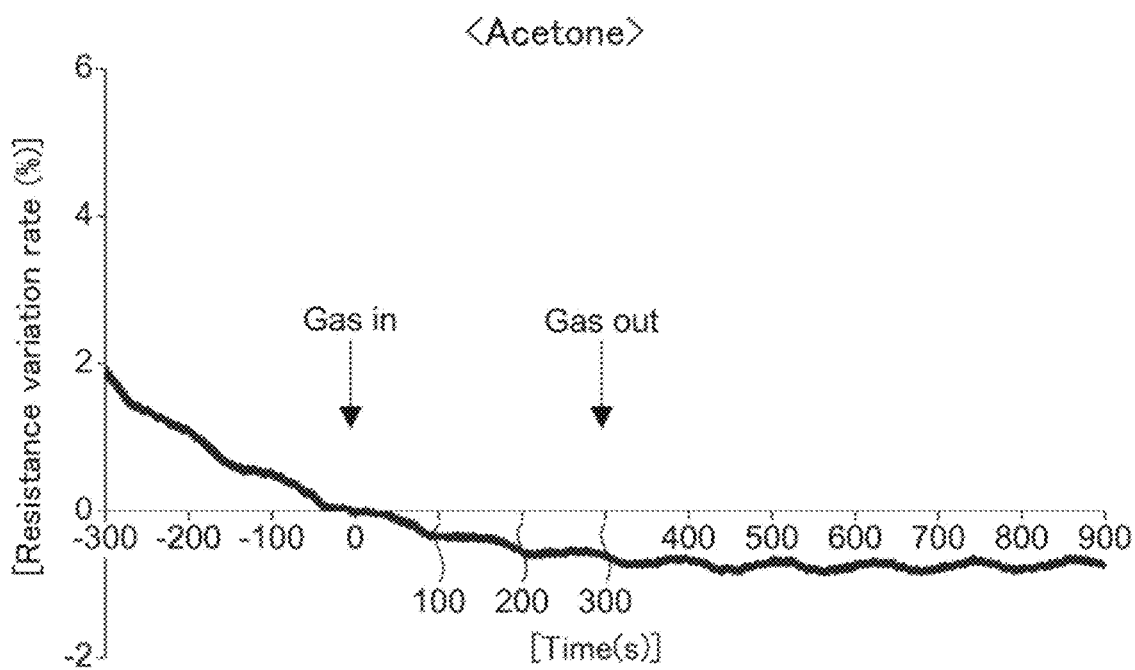
FIG. 6 is a view depicting an example of a response profile of the resistance of the gas sensor of the present embodiment to acetone whose atmospheric concentration is 20 ppm.

FIG. 3 is a view depicting an example of a response profile of the resistance of the gas sensor of the present embodiment to hydrogen sulfide whose atmospheric concentration is 0.8 ppm, and FIG. 4 is a view depicting an example of a response profile of the resistance of the gas sensor of the present embodiment to ammonium whose atmospheric concentration is 0.9 ppm. Further, FIG. 5 is a view depicting an example of a response profile of the resistance of the gas sensor of the present embodiment to ethanol whose atmospheric concentration is 20 ppm, and FIG. 6 is a view depicting an example of a response profile of the resistance of the gas sensor of the present embodiment to acetone whose atmospheric concentration is 20 ppm. It is to be noted that, in FIGS. 3 to 6, the axis of abscissa indicates time (Time (s: second)) and the axis of ordinate indicates the resistivity change rate (%).

As depicted in FIG. 3, while the electric resistance of the gas sensor 1 significantly varies with respect to hydrogen sulfide, it is recognized that a significant variation is not found in regard to ammonium, ethanol and acetone and very high gas species selectivity is indicated as depicted in FIGS. 4 to 6. In particular, it is recognized that, with the semiconductor material, gas sensor and gas measurement apparatus to which the gas sensor is applied described above, hydrogen sulfide (measurement target gas) in gas can be selectively detected with high sensitivity.

Figure 7:
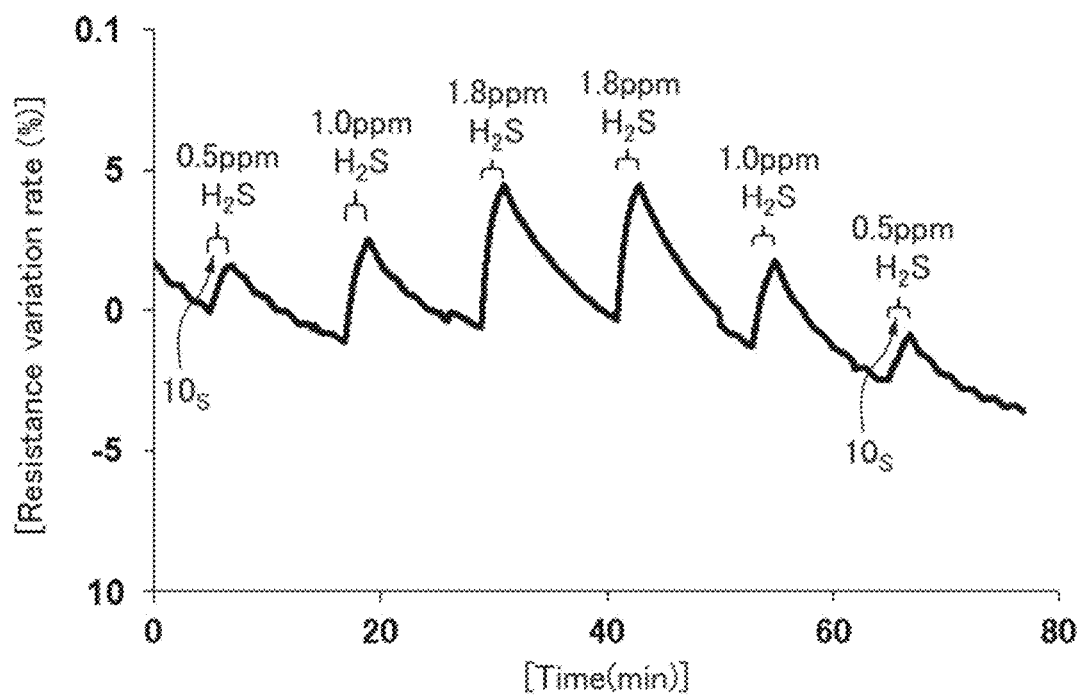
FIG. 7 is a view depicting an example of a response profile of the resistance of the gas sensor of the present embodiment to hydrogen sulfide whose atmospheric concentration is 0.5 ppm, 1.0 ppm and 1.8 ppm.
Figure 8:
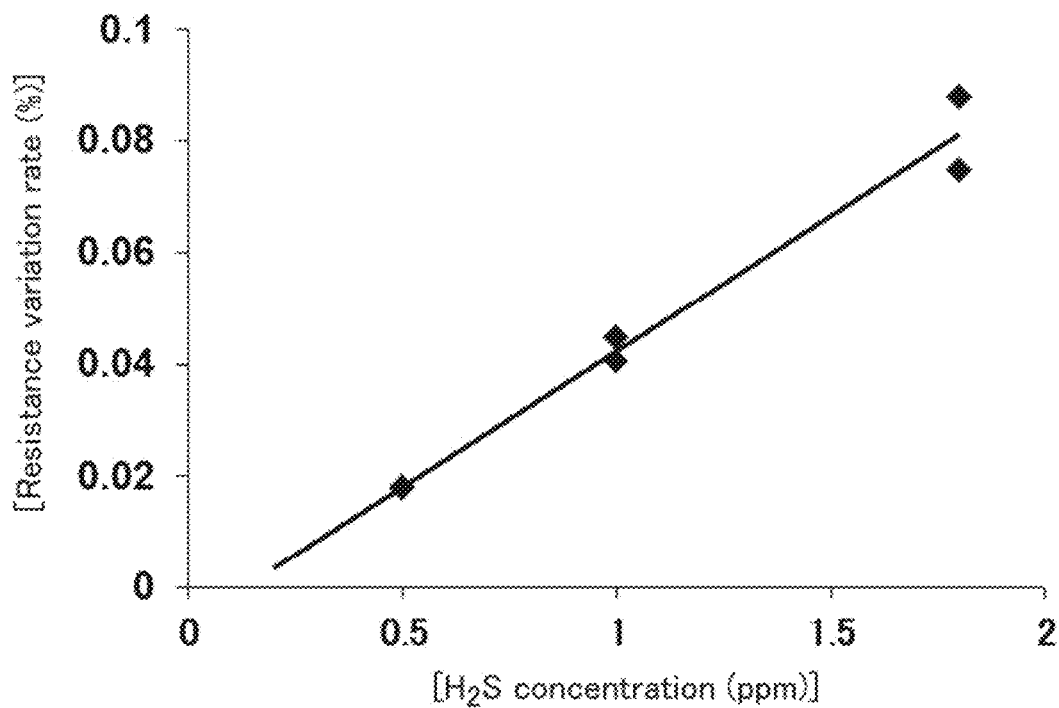
FIG. 8 is a view in which an inclination of time variation, within 10 seconds after start of contact with hydrogen sulfide, of a response profile of the resistance of the gas sensor of the present embodiment to hydrogen sulfide whose atmospheric concentration is 0.5 ppm, 1.0 ppm and 1.8 ppm is plotted with respect to the hydrogen sulfide concentration.

Now, a response when hydrogen sulfide whose concentration is varied is brought into contact with the gas sensor of the present embodiment and an inclination of the time variation of the resistivity change rate within a period of first 10 seconds in a response interval of concentration are described. FIG. 7 is a view depicting an example of a response profile of the resistance of the gas sensor of the present embodiment to hydrogen sulfide whose atmospheric concentration is 0.5 ppm, 1.0 ppm and 1.8 ppm. Further, FIG. 8 is a view in which an inclination of time variation, within 10 seconds after start of contact with hydrogen sulfide, of a response profile of the resistance of the gas sensor of the present embodiment to hydrogen sulfide whose atmospheric concentration is 0.5 ppm, 1.0 ppm and 1.8 ppm is plotted with respect to the hydrogen sulfide concentration. It is to be noted that, in FIGS. 7 and 8, the axis of abscissa indicates time (Time (s: second)) and the axis of ordinate indicates the resistivity change rate (%).

As depicted in FIGS. 7 and 8, it is recognized that the strength of a response by the gas sensor of the present embodiment is linear with respect to the concentration of hydrogen sulfide and that the strength of an initial response within 10 seconds after start of exposure indicates superior linearity with respect to the hydrogen sulfide concentration. In particular, it was confirmed that the gas sensor of the present embodiment is a high-sensitivity gas sensor having both of a quantitative performance and a high-speed performance.

Incidentally, a detection material film (detection body 14) was formed by applying and drying solution (semiconductor material) of PEDOT:PSS in which copper (II) bromide is included in concentration of 0.1 mol/L on a silicon wafer with an oxide film under conditions similar to those of the gas sensor of the present embodiment described above. When analysis by X-ray photoelectron spectroscopy was performed for the surface of the detection material film, it turned out that the ratio of the number of carbon atoms, number of oxygen atoms, number of sulfur atoms, number of copper atoms and number of bromine atoms on the surface was approximately 64:24:7:2:0.2 and the bromine was almost lost to approximately 1/10 with respect to the copper supplied from the copper (II) bromide.

Figure 9:
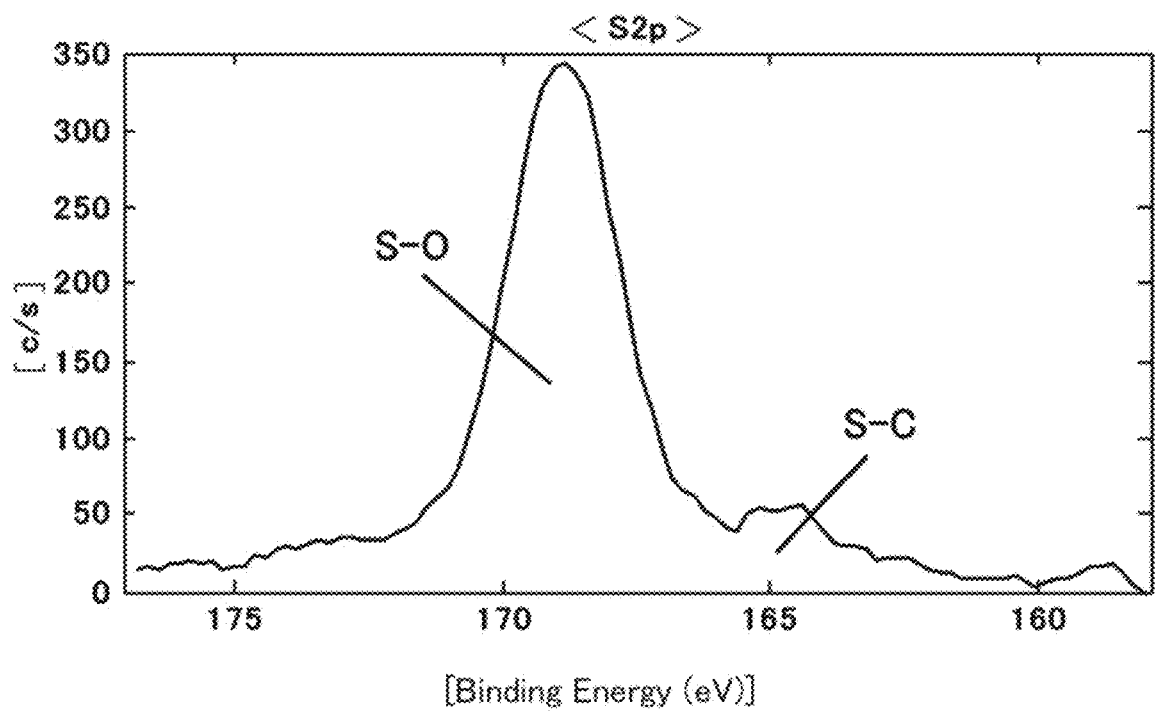
FIG. 9 is a view depicting an example of a narrow spectrum of S2p from within a result of X-ray photoelectric spectral analysis for a detection material film surface produced under similar conditions to those of the gas sensor of the present embodiment.

FIG. 9 is a view depicting an example of a narrow spectrum of S2p from among results of the X-ray photoelectron spectroscopy with regard to the surface of the detection material film produced under similar conditions to those of the gas sensor of the present embodiment. It is to be noted that the axis of abscissa indicates the Binding Energy (eV) and the axis of ordinate indicates the count number/second (c/s). In particular, it is considered that, since the ratio of sulfur atoms bonded to oxygen (S—O) corresponding to the number of configuration units of PSS and sulfur atoms bonded to carbon (S—C) corresponding to the number of configuration units of PEDOT is estimated to approximately 10:1 from the separation peak strength of the narrow spectrum of S2p depicted in FIG. 9, the number of copper atoms is approximately 1/3 that of sulfonic acid groups the PSS has.

Figure 10A:
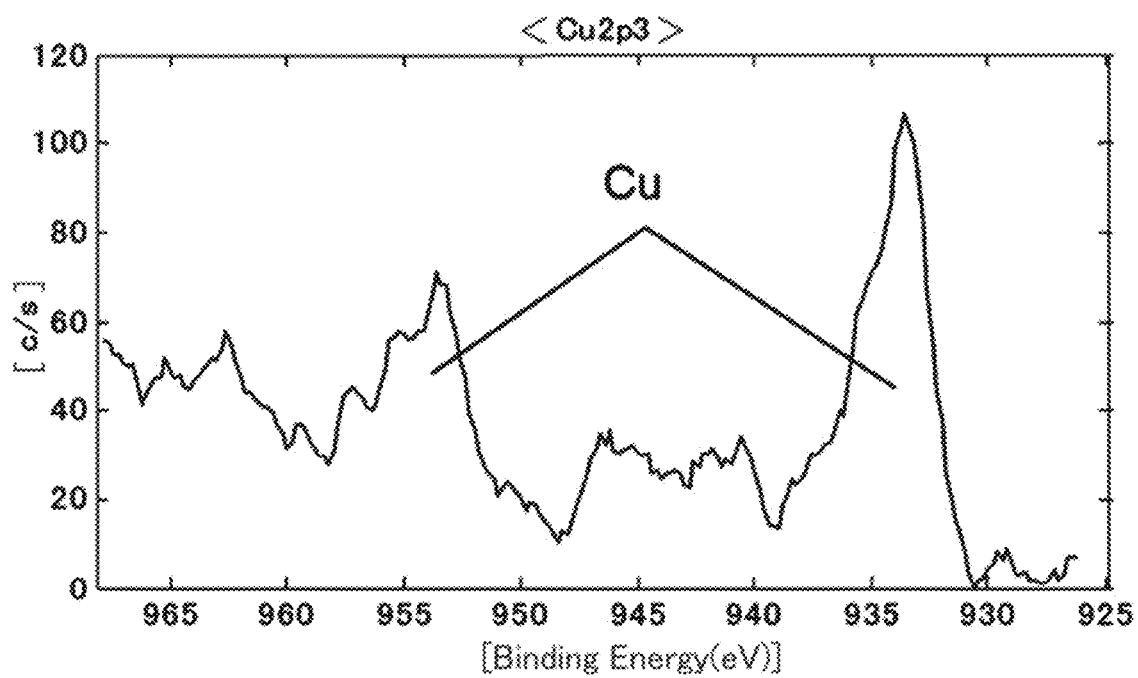
FIGS. 10A and 10B are views depicting an example of narrow spectrums of Cu2p3 and Cu 1 mm from within a result of the X-ray photoelectric spectral analysis for a detection material film surface produced under similar conditions to those of the gas sensor of the present embodiment.
Figure 10B:
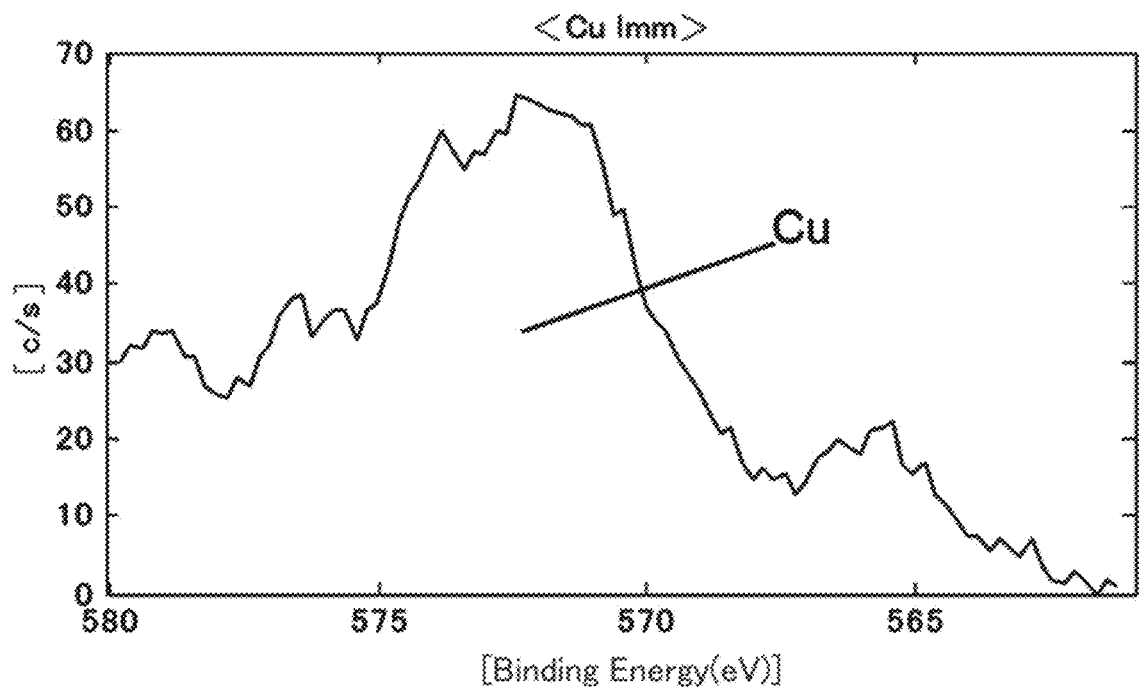

FIGS. 10A and 10B are views depicting an example of narrow spectrums of Cu2p3 and Cu 1 mm from among results of the X-ray photoelectron spectroscopy for the surface of the detection material film produced under similar conditions to those of the gas sensor of the present embodiment. Here, FIG. 10A depicts a narrow spectrum of Cu2p3 (right side from between two peaks), and FIG. 10B depicts a narrow spectrum of Cu 1 mm.

As depicted in FIG. 10A, at the main peak position of Cu2p3, the binding energy is approximately 934 eV. Further, as depicted in FIG. 10B, at the main peak position of Cu 1 mm, the binding energy is approximately 572 eV. Since the state of copper that satisfies both of them is monovalent copper ions bonded to sulfuric acids including sulfonic acid, it is considered that the copper is placed in a state in which it is bonded to sulfonic acid groups of PSS principally as monovalent ions.

Figure 11:
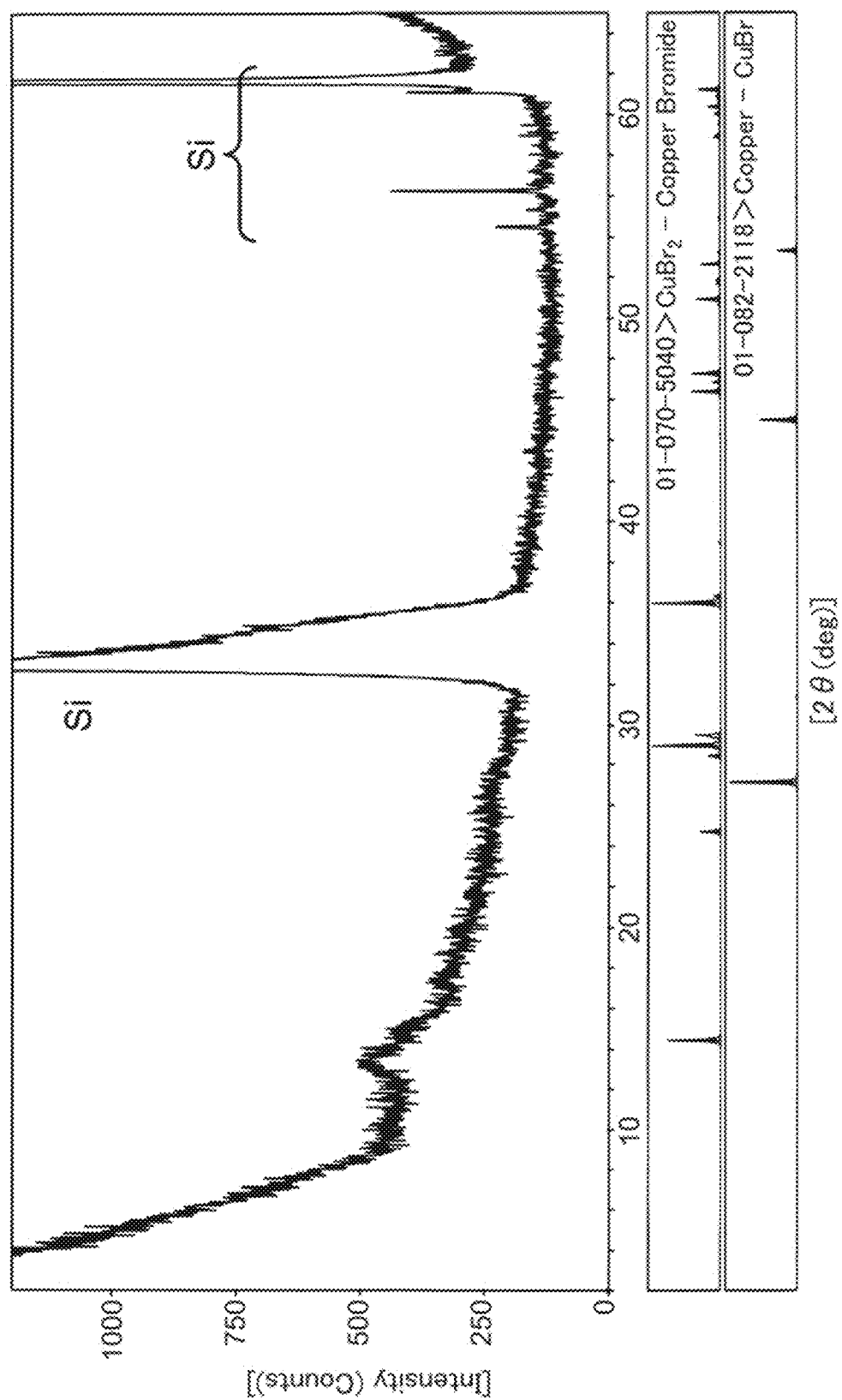
FIG. 11 is a view depicting an example of an X-ray diffraction profile in regard to a detection material film surface produced under similar conditions to those of the gas sensor of the present embodiment.

FIG. 11 is a view depicting an example of an X-ray diffraction profile (XRD: X-Ray Diffraction) in regard to the surface of a detection material film produced under similar conditions to those of the gas sensor of the present embodiment. As depicted in FIG. 11, it is recognized that only peaks originating from silicon (Si) of the substrate are observed and the semiconductor material that forms the detection material film produced under conditions similar to those of the gas sensor of the present embodiment (namely, the detection body of the gas sensor of the present embodiment) is amorphous.

FIGS. 12A and 12B are views depicting an example of an image of the surface of a detection material film produced under similar conditions to those of the gas sensor of the present embodiment by a typical scanning transmission electron microscope in the proximity of the center in the thickness wise direction and an example of mapping of an EDS signal corresponding to the K shell of Cu with respect to a same field of view. In particular, FIG. 12A depicts an example of an observation result (STEM image) by a scanning transmission electron microscope (STEM) of a cross section of a sample same as the sample of XPS (X-ray photoelectron spectroscopy) described hereinabove in the proximity of the center in the thickness wise direction. Meanwhile, FIG. 12B depicts an example of a mapping result of an EDS (Energy Dispersive X-ray Spectrometer) signal corresponding to the K shell of Cu, which was performed for a field of view same as that of the STEM image depicted in FIG. 12A.

First, as depicted in FIG. 12A, a detection material film (detection body of the gas sensor of the present embodiment) produced under conditions similar to those of the gas sensor of the present embodiment cannot detect a fine structure corresponding to crystal on the STEM image. Further, as depicted in FIG. 12B, according to a mapping result of the EDS signal corresponding to the K shell of Cu, a manner in which copper atoms are diffused substantially uniformly in the film is depicted, and it is recognized that, according to results of XPS, XRD and STEM and EDS mapping, monovalent copper ions are dispersed in the form bonded to PSS in the film without forming crystal.

Now, a comparative example with the embodiment (example) described hereinabove is described with reference to FIGS. 13 to 16. In this comparative example, a gas sensor of the comparative example corresponding to the gas sensor of the present embodiment described hereinabove was produced by a quite similar method except that copper (II) bromide was not added to solution of PEDOT:PSS, wherein detection body 14 was formed by applying and naturally drying a thin film of PEDOT:PSS on a silicon wafer with a thermal oxide film of 15 mm square on which Au electrodes 12 and 13 were produced.

A response of the gas sensor 1 to various gases (measurement target gases) was evaluated by placing the gas sensor of the comparative example produced in such a manner as described above into an air flow and changing over the gas source between pure air and one of various kinds of air including one of hydrogen sulfide of a concentration of 1 ppm, ammonium of a concentration of 1 ppm, ethanol of a concentration of 17 ppm and acetone of a concentration of 16 ppm. Here, the temperature of the used air was approximately 23° C. and the relative humidity was approximately 40%.

Figure 13:
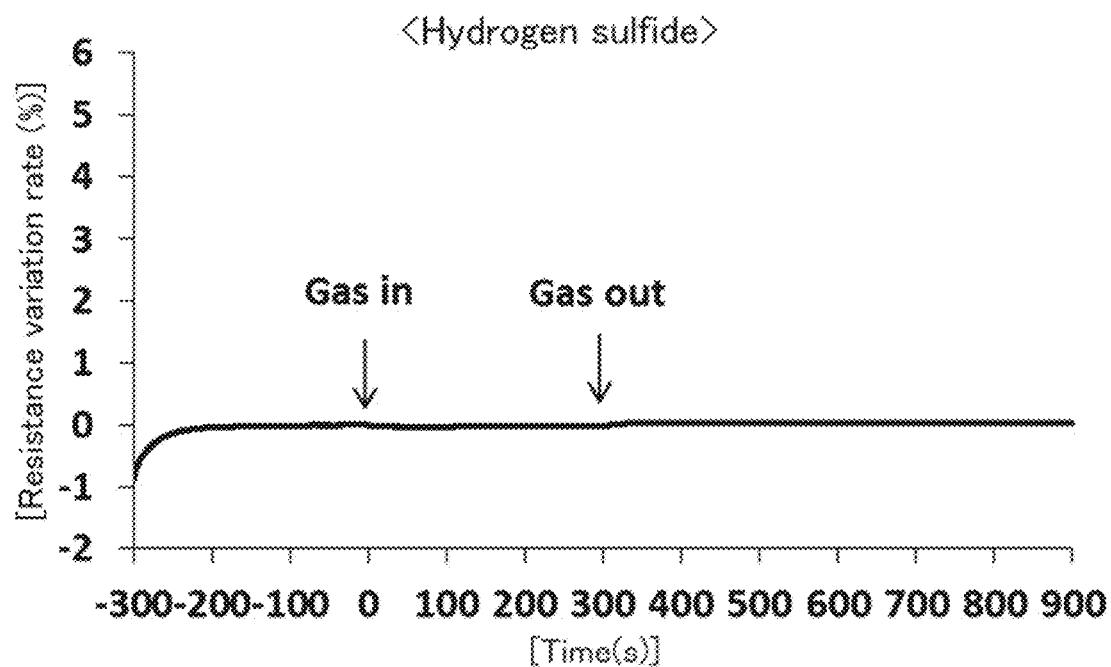
FIG. 13 is a view depicting an example of a response profile of the resistance of a gas sensor as a comparative example to hydrogen sulfide whose atmospheric concentration is 1 ppm.
Figure 14:
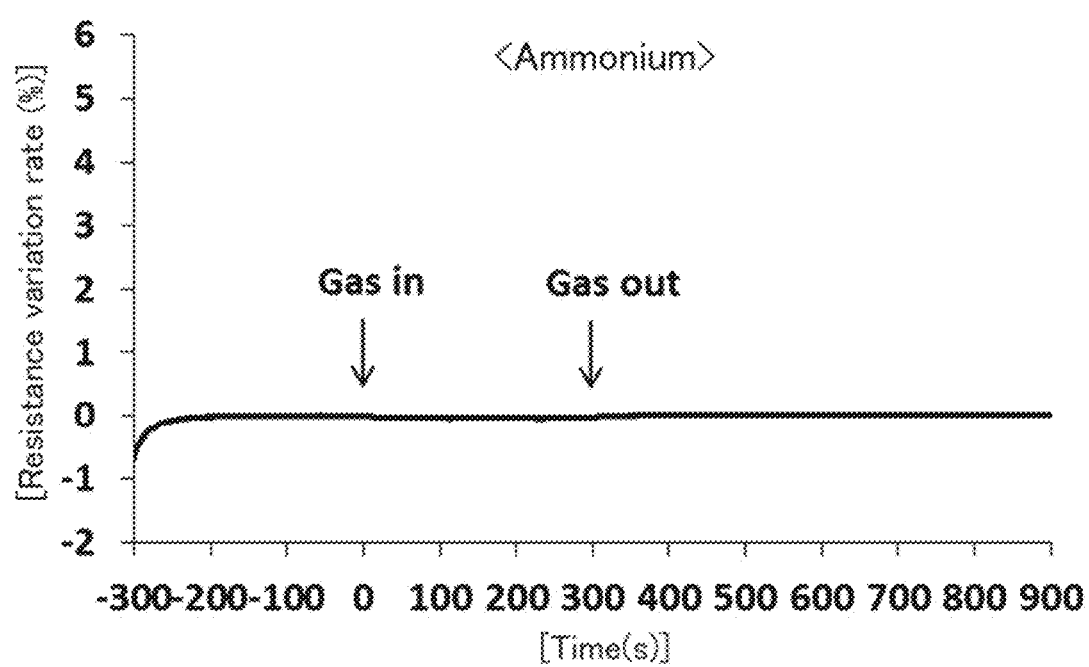
FIG. 14 is a view depicting an example of a response profile of the resistance of a gas sensor as a comparative example to ammonium whose atmospheric concentration is 1 ppm.
Figure 15:
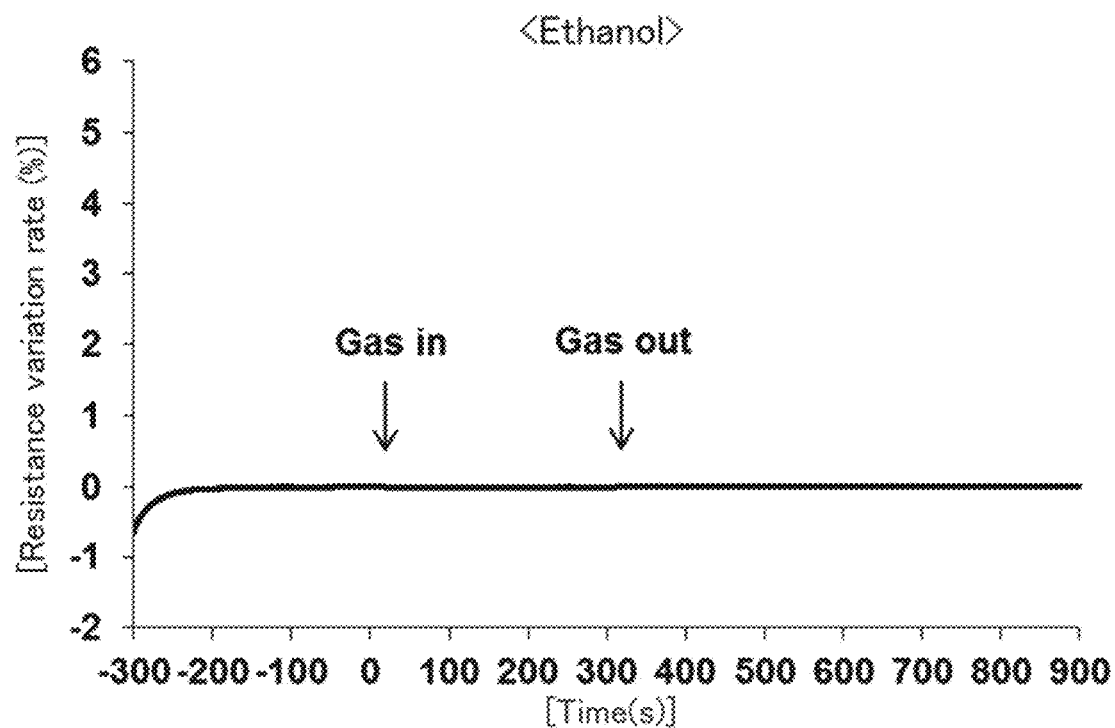
FIG. 15 is a view depicting an example of a response profile of the resistance of a gas sensor as a comparative example to ethanol whose atmospheric concentration is 17 ppm.
Figure 16:
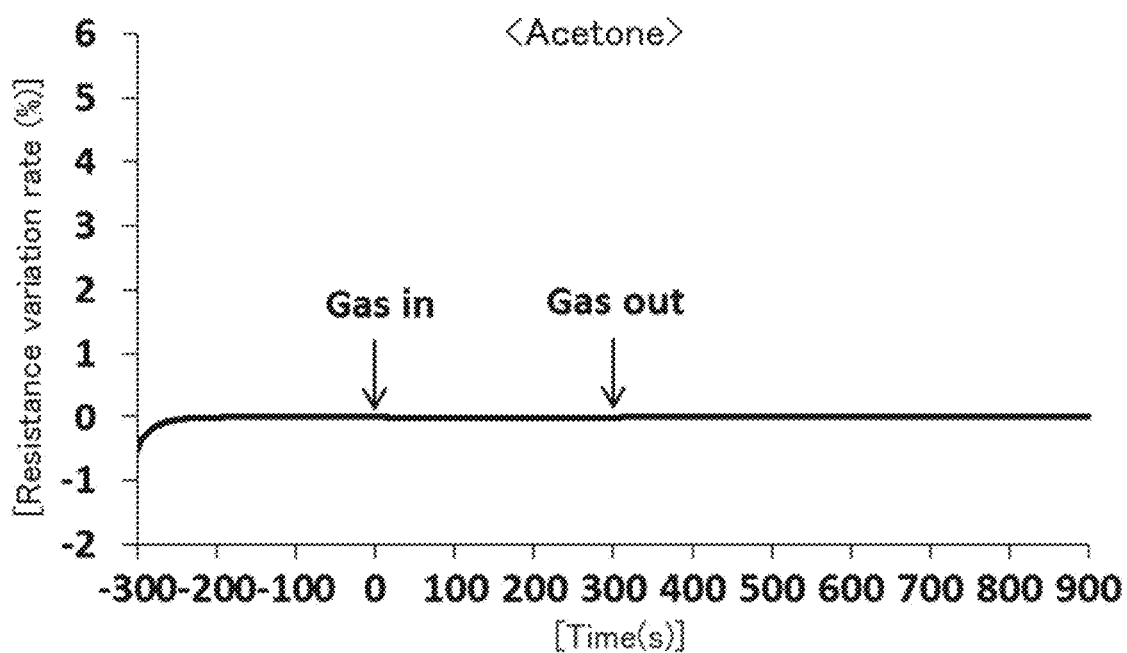
FIG. 16 is a view depicting an example of a response profile of the resistance of a gas sensor as a comparative example to acetone whose atmospheric concentration is 16 ppm.

FIG. 13 is a view depicting an example of a response profile of the resistance of the gas sensor as the comparative example to hydrogen sulfide whose atmospheric concentration is 1 ppm, and FIG. 14 is a view depicting an example of a response profile of the resistance of the gas sensor as the comparative example to ammonium whose atmospheric concentration is 1 ppm. Further, FIG. 15 is a view depicting an example of a response profile of the resistance of the gas sensor of the comparative example to ethanol whose atmospheric concentration is 17 ppm, and FIG. 16 is a view depicting an example of a response profile of the resistance of the gas sensor as the comparative example to acetone whose atmospheric concentration is 16 ppm. It is to be noted that, in FIGS. 13 to 16, the axis of abscissa indicates time (Time (s: second)) and the axis of ordinate indicates the resistivity change rate (%).

As apparent from comparison of FIGS. 13 to 16 and FIGS. 3 to 6 described hereinabove, it is recognized that, for example, different from the gas sensor of the present embodiment, the gas sensor of the comparative example in which copper (II) bromide is not added does not indicate such a significant resistance variation as exceeds a level of noise in regard to any gas (measurement target gas) including hydrogen sulfide, ammonium, ethanol and acetone. In particular, as apparent from comparison with a resistance variation to each gas by the gas sensor of the comparative example, the gas sensor of the present embodiment can detect, for example, hydrogen sulfide as measurement target gas selectively at a high speed and with high sensitivity by adding copper (II) bromide, which gives copper ions, for example, to polythiophene and sulfonic acid such that sulfonic acid is bonded to copper ions and especially monovalent copper ions are bonded to sulfonic acid. It is to be noted that it is a matter of course that, as the copper (II) bromide, other copper halides such as, for example, copper (II) fluoride, copper (II) chloride and copper (II) iodide can be used.

Although the embodiment has been described, all examples and conditions described herein are described for the object of helping to understand the invention and concepts of the invention applied to the technology, and especially the examples and the conditions described herein are not intended to restrict the scope of the invention. Further, such description of the specification does not indicate advantages and defects of the invention. Although the embodiment of the invention is described in detail, it is to be understood that modification can be made without departing from the spirit and scope of the invention.

All examples and conditional language provided herein are intended for the pedagogical purposes of aiding the reader in understanding the invention and the concepts contributed by the inventor to further the art, and are not to be construed as limitations to such specifically recited examples and conditions, nor does the organization of such examples in the specification relate to a showing of the superiority and inferiority of the invention. Although one or more embodiments of the present invention have been described in detail, it should be understood that the various changes, substitutions, and alterations could be made hereto without departing from the spirit and scope of the invention.

What is claimed is:

1. A gas sensor, comprising:
a detection body that is produced using a semiconductor material comprising polythiophene, sulfonic acid, and copper ion bonded to the sulfonic acid and that detects measurement target gas within gas.

2. The gas sensor according to claim 1, wherein
the copper ion includes monovalent copper ion and the monovalent copper ion is bonded to the sulfonic acid.

3. The gas sensor according to claim 1, wherein
the polythiophene includes poly 3,4-ethylene dioxythiophene and the sulfonic acid includes poly 4-styrene sulfonic acid.

4. The gas sensor according to claim 3, wherein
the semiconductor material is amorphous.

5. The gas sensor according to claim 1, wherein
copper(II) bromide is mixed in the semiconductor material and the semiconductor material is aqueous solution.

6. A fabrication method for the gas sensor according to claim 5, comprising:
producing a detection body by applying and drying the semiconductor material that is the aqueous solution.

7. The fabrication method according to claim 6, wherein
the gas sensor has a characteristic in which the gas sensor is likely to react to hydrogen sulfide but is less likely to react to any other materials.

8. The gas sensor according to claim 1, wherein
the gas sensor has a characteristic in which the gas sensor is likely to react to hydrogen sulfide but is less likely to react to any other materials.

9. A gas measurement apparatus, comprising:
the gas sensor according to claim 1, wherein, using the gas sensor, resistance variation of the detection body is observed to perform measurement of the measurement target gas.

10. The gas measurement apparatus according to claim 9, wherein
the gas measurement apparatus performs measurement of hydrogen sulfide.

11. A hydrogen sulfide concentration measurement method for measuring a concentration of hydrogen sulfide, comprising:
performing conversion into a concentration of the hydrogen sulfide based on a resistance variation rate of the detection body monitored as a function of time after contacting with the measurement target gas by the gas measurement apparatus according to claim 10.

* * * * *